United States Patent [19]

Fichera et al.

[11] Patent Number: 4,714,477
[45] Date of Patent: Dec. 22, 1987

[54] BALL-AND-SOCKET JOINT PROSTHESIS WITH BEARING INSERT

[75] Inventors: Alfred J. Fichera, Cordova; Samuel J. Chiarizzio, Memphis, both of Tenn.

[73] Assignee: Dow Corning Wright Corporation, Arlington, Tenn.

[21] Appl. No.: 894,589

[22] Filed: Aug. 8, 1986

[51] Int. Cl.$^4$ .............................................. A61F 2/34
[52] U.S. Cl. ...................................... 623/22; 623/18; 403/135
[58] Field of Search .................................. 623/16–23; 403/132, 133, 135, 141

[56] References Cited

U.S. PATENT DOCUMENTS

| | | | |
|---|---|---|---|
| 3,848,272 | 11/1974 | Noiles | 3/1 |
| 3,863,273 | 2/1975 | Averill | 3/1 |
| 3,978,528 | 9/1976 | Crep | 3/1.91 |
| 4,135,517 | 1/1979 | Reale | 623/22 |
| 4,241,463 | 12/1980 | Khovaylo | 3/1.913 |
| 4,380,090 | 4/1983 | Ramos | 3/1.912 |
| 4,408,360 | 10/1983 | Keller | 3/1.913 |
| 4,624,674 | 11/1986 | Pappas et al. | 623/22 |

OTHER PUBLICATIONS

"The OEC Universal Self-Aligning TM Acetabular Component", Brochure No. 01-50-1422, Orthopedic Equipment Co., Bourbon, Ind., 6 pages (product on sale in U.S. prior to Aug. 1985).
"Self-Centering TM Universal Hip", Brochure No. 382 0601-52, (Rev. 1), DePuy, Warsaw, Ind., 6 pages, (1982).
"Bi-Polar Articulating Components-Surgical Technique", Form No. Y-BMT-011/010184, Biomet, Inc., Warsaw, Ind., 5 pages, (1984).
"Bateman UPF TM II Universal Proximal Femur", Brochure No. SD-IUTS(421)NPI, 3M, St. Paul, Minn., 6 pages, (1982).

*Primary Examiner*—Richard J. Apley
*Assistant Examiner*—David J. Isabella
*Attorney, Agent, or Firm*—Richard E. Rakoczy

[57] ABSTRACT

A ball-and-socket joint prosthesis, e.g. a hip joint prosthesis, which comprises an outer shell element, a ball component, and a replaceable bearing insert element positioned between the shell and the ball component. The bearing insert has a generally spherical inside surface which encompasses more than half of the ball component to thereby retain it. The insert has an outside surface shaped to mate with the inside surface of the shell, and the shell element and the insert element have a locking mechanism consisting of a protruding portion which extends a major distance around a side surface of one element which locks into a mating depression in the other element. In a preferred embodiment, the insert is horizontally slotted around a major portion, but less than the entire distance around the insert, above that portion of the locking mechanism present on the insert and is vertically slotted from the bottom of the insert to the horizontal slot thereby forming at least one, but preferably two, movable finger(s). The flexibility of the finger(s) allows the ball component to be inserted into and removed from the insert. Once the insert containing the ball component is locked into the shell, the vertical slot may be at least partially closed by moving the finger(s) to disengage the locking mechanism and allow removal of the insert and the ball component from the shell.

10 Claims, 6 Drawing Figures

BALL-AND-SOCKET JOINT PROSTHESIS WITH BEARING INSERT

BACKGROUND OF THE INVENTION

The present invention relates to surgically implantable prosthetic bone joints and more particularly to prosthetic ball-and-socket bone joint devices having a replaceable bearing insert present in the socket on which the ball articulates.

Disease or trauma involving the bones of a joint could necessitate that the natural joint be partially or wholly replaced by implanting a joint prosthesis. Joint prostheses have been developed to replace natural ball-and-socket joints, such as those found in the shoulder and the hip.

For example, for restoration of a hip joint, a prosthesis typically consists of a femoral component which includes a stem adapted to be introduced into a surgically prepared intramedullary canal of a femur, a neck attached to the proximal end of the stem portion, and a head portion attached to the neck. The head portion could be designed to articulate with the concave portion of the acetabulum or with a concave acetabulum component secured to the acetabulum, either of which constitute the socket.

It is known in the art that articulation can be improved by incorporating a component of low friction material to serve as one of the articulating surfaces. Providing for substantially frictionless articulation allows for easier movement of the joint, decreased torsional stresses and their effects on the joint components, extended implant life, and less pain for the patient.

Several designs developed make use of a low-friction material, e.g. ultra-high molecular weight polyethylene (UHMWPE), to comprise one of the articulating surfaces. Some of these designs include a ball component on the neck of the femoral component, a low-friction bearing surface surrounding a portion of the ball on which the ball articulates, and an outer shell permanently retaining the bearing surface. These prostheses can be assembled merely by popping the ball component into the bearing-lined outer shell. The bearing inner surface is generally spherical to mate with the ball component and, if the bearing surface and/or the outer shell surrounds more than half of the ball, the ball is retained inside the outer shell. These designs risk separation of the ball component from the outer shell if insertion and removal of the ball component is relatively easy.

If the device is designed so that the ball component is not easily separated, then a relatively large amount of force is required to insert the ball component, making it difficult for the surgeon to insert and more painful for the patient. Alternatively, the procedure of assembly may include heating the plastic insert to allow it to expand for insertion of the ball component. This adds an additional and time-consuming step during surgery. With these types of prostheses subsequent operations to remove the ball component to revise the joint are difficult, possibly requiring removal of the femoral stem if separation of the ball from the bearing component is too difficult.

In an attempt to lower the risk of separating the ball component from the shell yet ensure that revision of the hip joint with different prosthetic components is possible without having to remove the stem from the femur, several designs have been developed that make use of a bearing component with a means for locking and unlocking the ball component.

Designs which have non-replaceable inserts include those disclosed in U.S. Pat. Nos. 4,408,360 and 4,241,463. Non-replaceable inserts have the disadvantage of requiring replacement of both the outer shell and the insert after wear of the insert or for revision to a different size outer shell.

Prostheses with replaceable inserts of multiple components have been disclosed in U.S. Pat. No. 4,380,090 to Ramos, U.S. Pat. No. 3,848,272 to Noiles and U.S. Pat. No. 3,978,528 to Crep. Replaceable inserts are those that allow for assembly and disassembly of the entire prosthesis with little or no damage to the insert. Ramos discloses a three-component insert which includes a bearing insert, an annular bearing, and a retaining ring. Noiles shows an embodiment that includes two inserts and a flexible ring member. Another embodiment shown by Noiles is a one- or two-piece insert that is threaded for screwing into the acetabulum prosthesis. Crep shows a split lining (two-piece) insert and a locking ring. The multiple-piece inserts have the disadvantages of having multiple pieces to assemble and account for and having the potential that several pieces would be loose inside the body if dislocation occurred. The threaded inserts of Noiles are heated to cause expansion in order for the hip ball to be popped in and further risk gradual unthreading or loosening of the insert during use.

Two-piece bearing inserts have been developed by Orthopedic Equipment Company (OEC), DePuy, and Biomet Inc. These inserts not only require the manufacture and assembly of the two pieces, but also risk having two insert pieces loose in the body in the event of dislocation. The loose pieces could cause damage to the body internally and would preclude external reduction.

Orthopedic Equipment Company sells OEC Universal Self-Aligning Acetabular Components, as shown in Form No. 01-50-1422, which includes two pieces: a UHMWPE inner bearing and a split titanium retaining ring. The inner bearing is slotted twice from the bottom of the bearing to the apex leaving a hinged portion at the apex, and the retaining ring is fitted into a groove on the outside of the bearing. When the prosthesis is assembled, the retaining ring is also locked into a groove in the inside of a metal outer bearing. During disassembly, removal of the inner bearing from the outer bearing requires a specially-made releasing ring.

Biomet Incorporated sells components under the name BI-POLAR Articulating Components, and in Brochure No. Y-BMT-011/010184 (1984), "BI-POLAR Articulating Components - Surgical Technique", the components are described as a metal outer shell with an UHMWPE surface fitted inside the shell which is secured to the femoral implant head by means of a slotted UHMWPE locking ring. The outside of the ring has contours and locking ridges to match the inner shell and fits below the centerline of the femoral head. Assembly of the prosthesis is by first placing the locking ring over the femoral head, sliding on the shell, then securing the shell to the locking ring. For disassembly, the locking ring can be released by inserting instrument tips in the holes in the locking ring and compressing the slot closed.

DePuy, a division of Boehringer Mannheim Corporation, sells a hip prosthesis under the name, Self-Centering ® Universal Hip shown in Brochure 382 0601-52

(Rev. 1) (1982), which includes an outer metal cup with an inner annular groove, a polyethylene insert, and a locking ring. The polyethylene insert is generally hemispherical on its outside and inside surfaces with a deep annular groove on the outside near the bottom or open end of the insert. The locking ring is slotted vertically and has an annular rib on the outside surface and an annular lip on the inside surface at the top of the ring designed to fit into the groove of the insert. Assembly is accomplished by connecting the insert and the locking ring together and snapping the assembly onto the femoral component head and sliding the metal cup over the assembly. The annular rib on the locking ring locks into the metal cup's annular groove. For disassembly, release forceps are inserted into holes in the bottom of the locking ring to close the slot, thus releasing the rib from the groove. To make this insert assembly, narrow design tolerances are required for a secure fit between the locking ring and the insert.

The two-piece bearing inserts described above not only require the manufacture and assembly of two insert pieces, but also risk having two insert pieces loose in the body in the event of dislocation. The loose separated pieces could cause further damage to the body internally and would preclude external reduction.

3M sells a femoral head prosthesis by the name of Bateman UPF® II that has a one-piece polyethylene bearing insert. Brochure No. SD-IUTS(421)NPI (1982) shows that the interlock between the outer head rim and the insert segments is accomplished by a lip on the bottom inside of the outer head rim seating into a notch on the outside bottom of the bearing insert. On the outside surface of the side of the insert there is an annulus forming a recess. The insert is slotted from the bottom to the annulus in six places, thereby forming six solid segments. The insert encompasses more than one-half of the metal head to retain it. Removal of the outer head is accomplished by (1) inserting tool or bone screws into two holes in two opposing segments of the bearing insert, (2) pressing the holes together slightly to disengage the interlock, and (3) slipping the outer head off. The product brochure indicates that this prosthesis design is covered in U.S. Pat. No. 3,863,273. A prosthesis with an easier method of disassembly is still desired.

SUMMARY OF THE INVENTION

Objects of the present invention are to provide a low-friction ball-and-socket joint prosthesis that (1) is relatively simple to manufacture, (2) is quickly and easily assembled, requiring minimal force, (3) is designed so that the ball component does not easily dislocate from the outer shell, (4) is designed so that the ball is easily and quickly removed from the outer shell when desired, e.g. for revision or refitting, so that the procedure does not require removal of the stem portion from the long bone, (5) is designed so that if separation of the ball component from the outer shell occurs, external reduction may be possible, and (6) has a one-piece bearing component to reduce the number of parts to assemble and account for and, once implanted, if separation of the bearing insert from the prosthesis occurred, a minimal number of plastic components would be loose inside the body.

The invention provides a ball-and-socket joint prosthesis which comprises an outer shell element, a generally spherical ball component that fits within the outer shell, and a bearing insert element which is positioned between the outer shell and the ball component. The bearing insert is open-ended at its bottom and opens to a generally spherical inside surface with dimensions being such that after insertion of the ball component, the ball component is allowed to freely swivel yet is retained within the insert. The outside surface of the insert is shaped to mate with the inside surface of the shell. To lock the insert into the shell and more securely retain the ball component, the shell element and the bearing insert element have a locking mechainism consisting of a protruding portion on a side surface of one element and extending a major distance around the element for locking engagement with an opposed mating depression in the other element. The insert has a substantially horizontal slot, situated above that portion of the locking mechanism present on the insert, which slot extends around a major portion of the insert but less than the entire periphery of the insert to thereby provide a connecting portion. The insert further has a single slot extending from the bottom of the insert up to the horizontal slot to form at least one movable finger attached to the rest of the insert by the connecting portion. The single slot has sufficient width and each finger has dimensions relative to the ball component to permit removal of the insert containing the ball component from the shell when the single slot is at least partially closed through the use of a means on the insert for moving at least one finger and permitting at least partial closure of the single slot.

In a more preferred embodiment, the prosthesis is a total hip prosthesis and further includes a stem portion which is attached to the ball component by means of a neck component. The insert of the preferred embodiment further includes two fingers of substantially equal length, each provided with a bore through the bottom surface for insertion of an instrument to move the fingers closer together.

BRIEF DESCRIPTION OF THE DRAWINGS

The above and other objects and advantages of the present invention will become apparent to those skilled in the art upon an examination of the following description and drawings which are illustrative of the present invention.

In the Drawings.

DETAILED DESCRIPTION OF THE INVENTION

Figure 1:
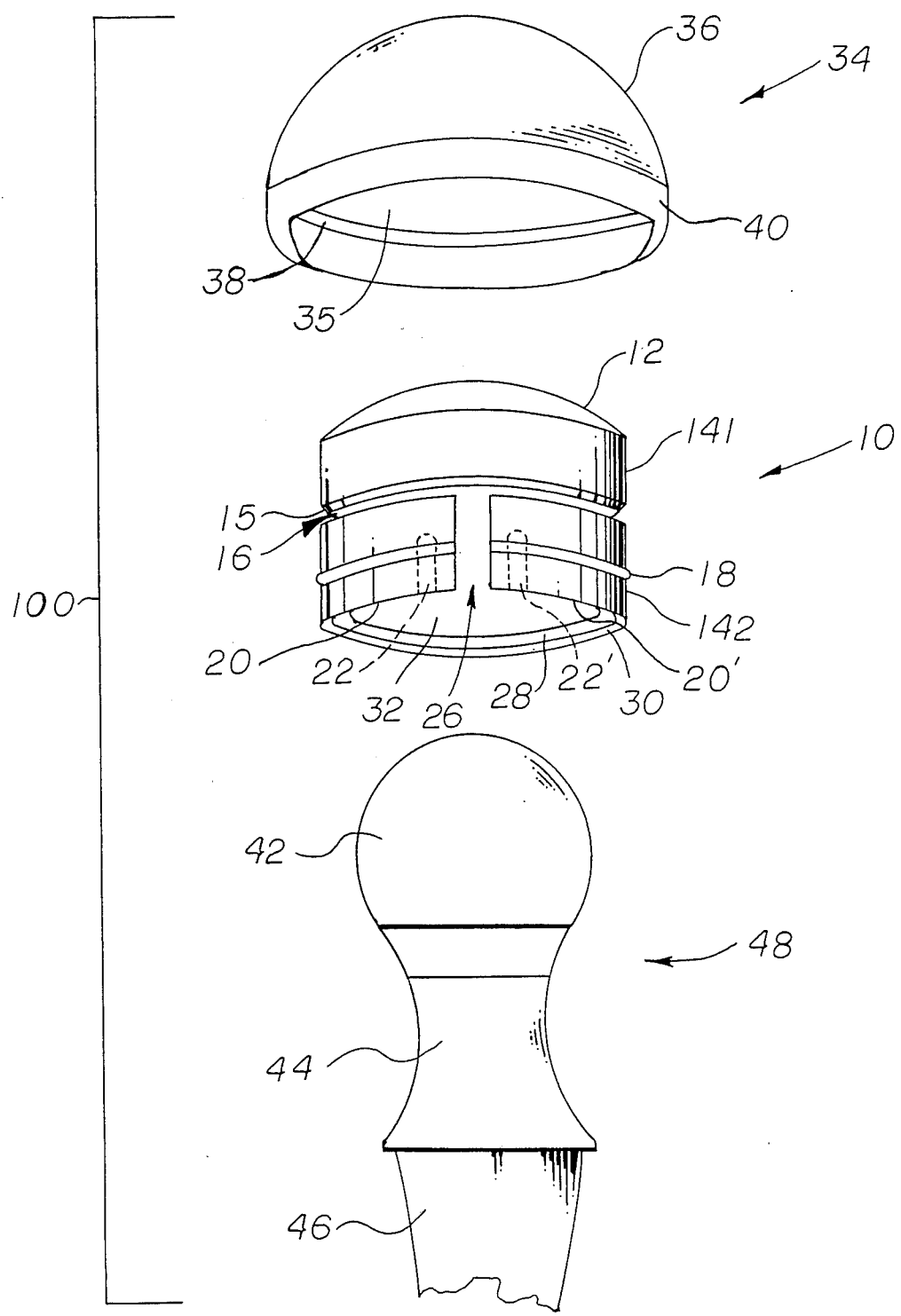
FIG. 1 is an exploded perspective view of total hip prosthesis 100 according to the present invention.
Figure 2:
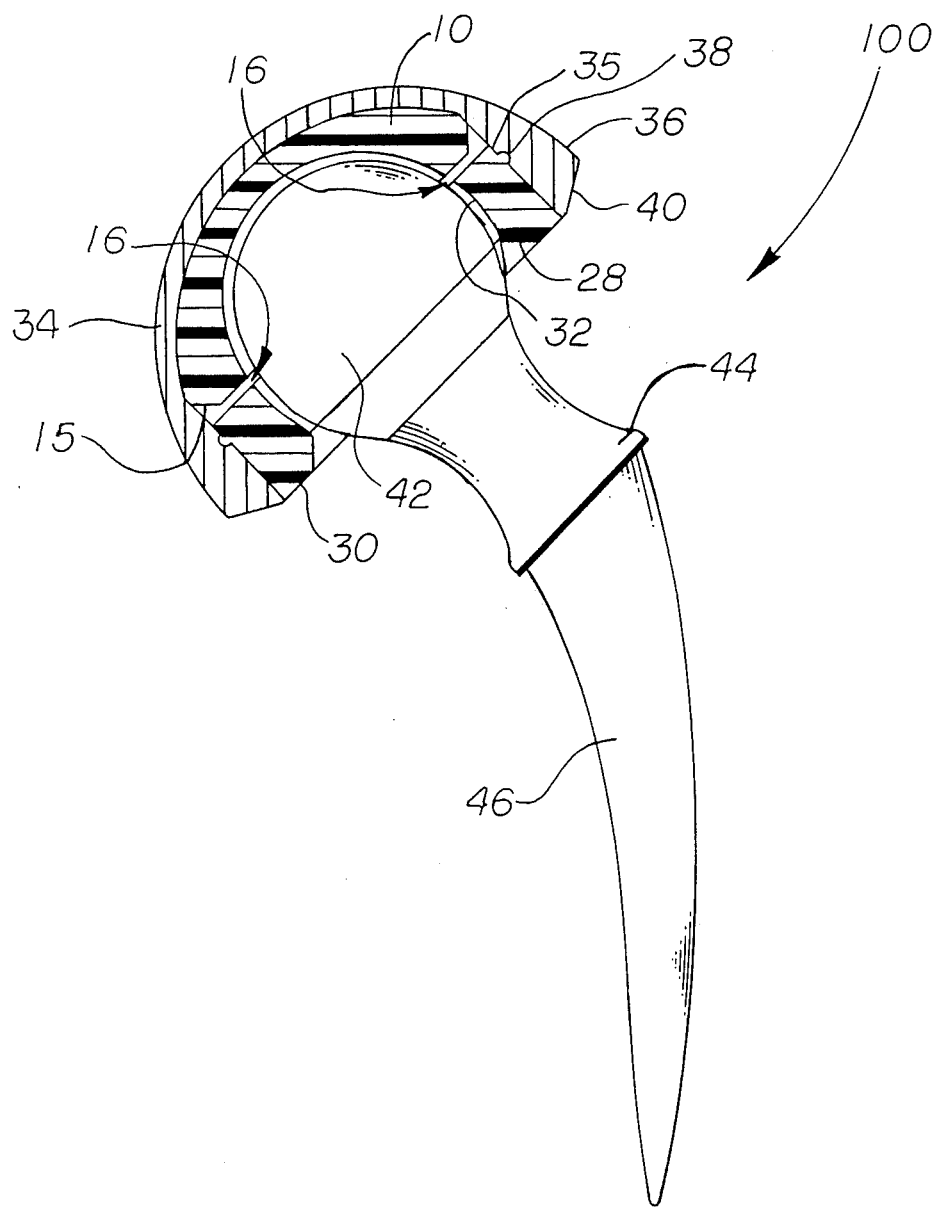
FIG. 2 is an elevational view in partial cross-section of total hip prosthesis 100 of FIG. 1.
Figure 3:
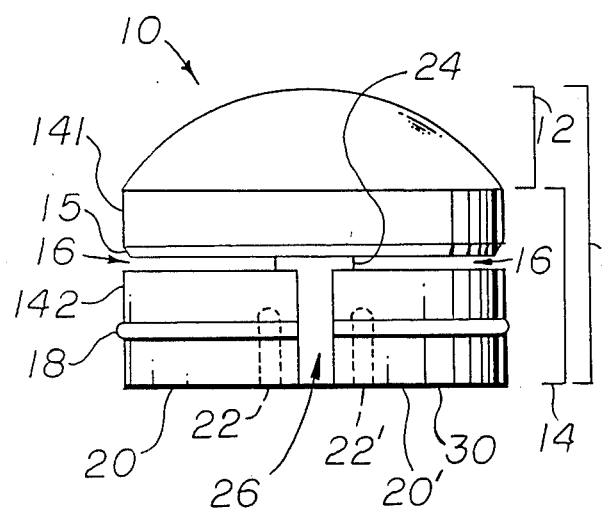
FIG. 3 is a front elevational view of bearing insert 10 shown in FIG. 1.
Figure 4:
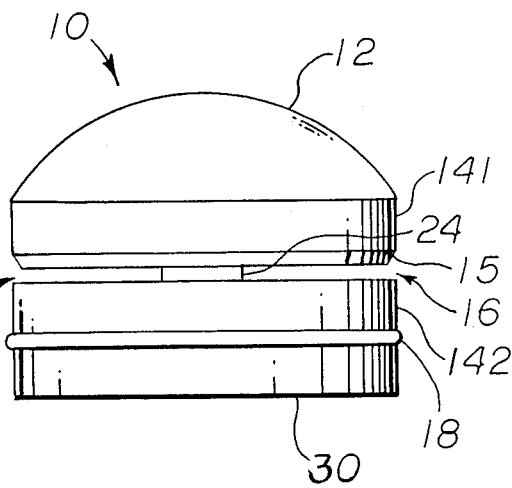
FIG. 4 is a back elevational view of bearing insert 10.
Figure 5:
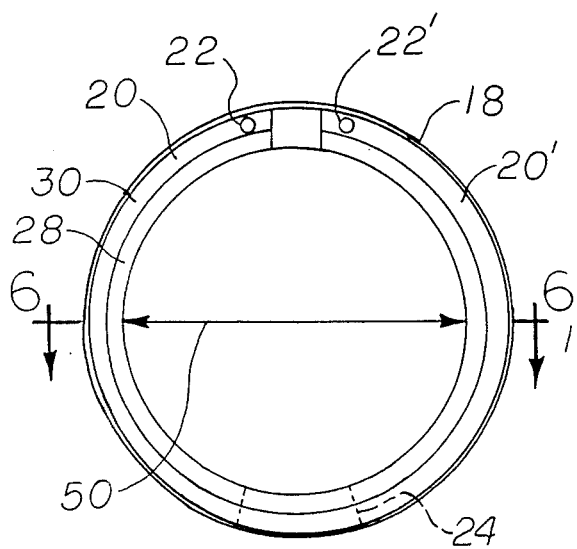
FIG. 5 is a bottom view of bearing insert 10.
Figure 6:
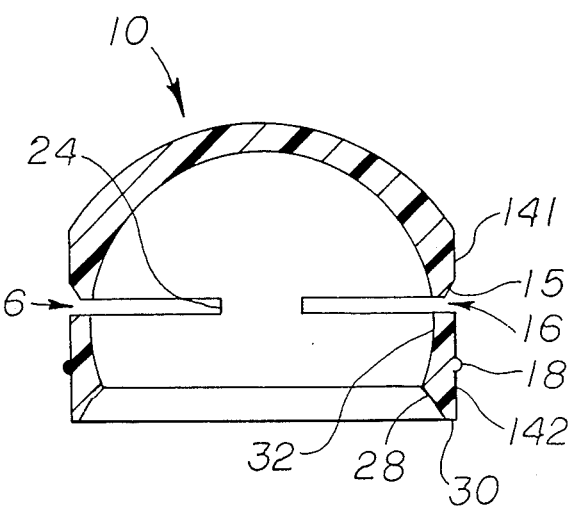
FIG. 6 is a partial cross-sectional view of bearing insert 10 taken along lines 6—6 of FIG. 5.

Referring to the Drawings, wherein like reference characters designate corresponding parts throughout the Figures thereof, FIGS. 1 and 2 depict a preferred form of a ball-and-socket prosthesis according to the invention in the form of total hip prosthesis 100 which is composed of outer shell 34, bearing insert 10, and femoral component 48. FIG. 1 is an exploded, perspective view of prosthesis 100, and FIG. 2 is an elevational view in partial cross-sectional of assembled prosthesis 100. As can be seen in FIG. 2, when assembled, ball component 42 of femoral component 48 fits inside bearing insert 10 which fits inside outer shell 34.

Femoral component 48 is composed of stem 46 which is connected to ball component 42 by means of neck 44. The stem 46 is designed to be implanted into a surgically-prepared intramedullary canal of a femur (not shown). Ball component 42 is generally spherical and, when assembled to form prosthesis 100, is designed to articulate with inside surface 32 of bearing insert 10.

Bearing insert 10, as shown in FIGS. 1-6, has outside surface 11 defined by spherical upper portion 12 and cylindrical lower portion 14 and an inside surface that is primarily spherical, shown as 32, and has bevelled surface 28 near the open-ended bottom of bearing insert 10. Outside surface 11 is shaped to mate with inside surface 35 of outer shell 34. Spherical inside surface 32 of bearing insert 10 mates with ball component 42, thus allowing for articulation between ball component 42 and inside surface 32. Inside surface 32 surrounds more than half of ball component 42 thereby retaining ball component 42 inside bearing insert 10. The diameter of inside surface 32 is slightly larger than the diameter of ball component 42 to facilitate unlocking of the locking mechanism which will be described later.

Near the open-ended bottom of bearing insert 10, inside surface 28 is bevelled for easier insertion of ball component 42 and provides ball component 42 a greater range of swivelling once it is inserted.

Through cylindrical portion 14 of bearing insert 10, there is horizontal slot 16 that extends circumferentially around a major portion of bearing insert 10 leaving connecting portion 24 connecting portion 141 above and portion 142 below horizontal slot 16. Below horizontal slot 16 is annular rib 18 on the outside surface of portion 142 which extends circumferentially around a major portion, and preferably all, of portion 142 and mates with annular groove 38 in inner surface 35 of outer shell 34, the mating of which can best be seen in FIG. 2. This mating is the means for locking bearing insert 10 into outer shell 34. On the outside of the insert 10, directly above horizontal slot 16, bevelled surface 15 is provided to prevent the upper edge of slot 16 from catching on the lower edge of annular groove 38 during removal of insert 10 from outer shell 34.

Across from connecting portion 24 of bearing insert 10 is vertical slot 26 which extends from flat bottom 30 to horizontal slot 16 thereby creating two essentially equal-length movable fingers 20 and 20'. When insert 10 is inserted in shell 34, the distance indicated by arrows 50 is less than the maximum diameter of ball component 42 to thereby retain component 42 within insert 10. Movable fingers 20 and 20' can flex slightly to expand the diameter of the opening of the bearing insert 10, thereby allowing insertion and removal of larger diameter ball component 42, when desired. At the underside of fingers 20 and 20' are bores 22 and 22' near vertical slot 26, as can best be seen in FIG. 5. Bores 22 and 22' are present so that, after bearing insert 10 is locked into outer shell 34, instrument tips, e.g. forcep tips (not shown), may be inserted into bores 22 and 22', compressed together so as to close, at least partially, vertical slot 26; such closer is possible because of the dimensions of the fingers 20 and 20' relative to the ball component 42. As a result, protruding rib 18 of bearing insert 10 is removed from annular groove 38 in outer shell 34, thus, permitting easy removal of bearing insert 10 from outer shell 34.

Outer shell 34 has generally spherical outside surface 36 with bevelled portion 40 near the bottom opening. Spherical outside surface 36 is designed to articulate with a corresponding spherical concave portion of an acetabulum (not shown). Bevelled portion 40 smooths the outer shell's edges to reduce the potential for tissue damage caused by the movement of outer shell 34 in the acetabulum.

In an alternative embodiment, when the patient's acetabulum is perceived to be too damaged or diseased to serve as a surface for articulation, outer shell 34 is constructed to permit secure attachment to the acetabulum by means known in the art, such as by including cementing or anchoring projections on outer shell 34 to permit fixation to the acetabulum. In this design, the only means for articulation is between ball component 42 and the inside surface 32 of the bearing insert 10.

As known, however, if the acetabulum is in such a condition so as to serve as an articulating surface, the outer shell 34 is preferred to be designed to articulate within the acetabulum, therefore, providing for a dual articulating prosthesis: articulation between outer shell 34 and the acetabulum and articulation between ball component 42 and inside surface 32 of bearing insert 10.

Assembly of the prosthesis as shown in FIGS. 1 and 2 is by (1) inserting ball component 42 into bearing insert 10 and then (2) inserting bearing insert 10 into outer shell 34. Separation of the components is accomplished by (1) inserting instrument tips into bores 22 and 22', (2) compressing the bores closer together thereby releasing protruding rib 18 from annular groove 38, (3) removing bearing insert 10 from outer shell 34, and (4) pulling ball component 42 out of bearing insert 10.

The outer shell and the femoral component is constructed of biocompatible materials possessing a sufficient amount of strength to function in the application. For example, the outer shell and the femoral component may be constructed of cobalt/chrome/molybdenum alloy or titanium alloy, as is known in the art. The bearing insert is constructed of a low-friction biocompatible material, e.g. ultra-high molecular weight polyethylene.

Other modifications and variations of the ball-and-socket prosthesis of the present invention are possible and will become apparent to those skilled in the art upon an examination of the above Specification and Drawings. For example, the outside surface of the bearing insert may be cylindrical or hemi-spherical instead of cylindrical with a spherical portion as shown in the Drawings.

Alternatively, the means for locking the insert into the outer shell could be reversed so that the groove is on the insert and the protruding rib is on the inside surface of the outer shell. To facilitate insertion and removal of the insert in the shell, in such an embodiment, the insert could be slotted vertically from the bottom to the apex of the insert thereby providing the flexibility needed by the non-fingered portion of the insert to permit it to pass over the rib.

The bottom of the insert could extend below the outer shell or not extend as far as the outer shell. If the insert extended below the outer shell, the bores could be positioned on the side of the insert. Means to close the vertical slot, other than the means using bores, could be used, e.g. outwardly extending tabs could be provided for grasping and compressing the slot closed. The fingers on the insert may have a wider protruding rib than that shown or may have multiple protruding ribs. There may be only one movable finger, instead of two as shown, so that the connecting portion is adjacent the vertical slot and, to facilitate closing the vertical slot, a bore is provided in the bottom surface of the finger and in the bottom surface on the opposite side of the vertical slot. There may also be provided a locking mechanism, such as vertical protrusions and matching grooves, between the outer shell and the insert to keep the insert from rotating within the shell.

These and other variations of the present invention may be made which fall within the scope of the appended claims even though such variations were not specifically discussed above.

That which is claimed is:

1. A ball-and-socket joint prosthesis which comprises:
 (A) a shell element having an inside surface and an outside surface; and
 (B) a generally spherical ball component for insertion within
 (C) a bearing insert element which is open-ended at its bottom, the bottom of the insert opening to a generally spherical inside surface for receiving the ball component, the insert having an outside surface which is shaped to mate with the inside surface of the shell, the dimensions of the inside surface of the insert being such that after insertion, the ball component is allowed to freely swivel, but is retained within the insert after the insert containing the ball component is locked within the shell,
 the shell element and the insert element having a locking mechanism consisting of a protruding portion extending a major distance around a side surface of one element for locking engagement with an opposed mating depression in the other element,
 the insert having a substantially horizontal slot, situated above that portion of the locking mechanism present on the insert, which slot extends around a major portion of the insert but less than the entire periphery of the insert to thereby provide a connecting portion;
 the insert having a single slot extending from the bottom of the insert up to the horizontal slot to thereby form at least one movable finger attached to the remainder of the insert by the connecting portion, the single slot having a sufficient width and each finger having dimensions relative to the ball component to permit removal of the insert containing the ball component from the shell when the single slot is at least partially closed through use of
 a means on the insert for moving at least one finger and permitting at least partial closure of the single slot.

2. The prosthesis as defined in claim 1 wherein the protruding portion is on the outside surface of the insert and the depression is in the inside surface of the shell.

3. The prosthesis as defined in claim 1 wherein the vertical slot forms two fingers of substantially equal length.

4. The prosthesis as defined in claim 3 wherein the fingers are each provided with a bore through the bottom surface for insertion of an instrument to move the fingers closer together.

5. The prosthesis as defined in claim 1 wherein the prosthesis is a total hip prosthesis and further includes a neck portion attached to the ball component and a stem attached to the neck.

6. The prosthesis as defined in claim 5 wherein the protruding portion is on the outside surface of the insert and the depression is in the inside surface of the shell.

7. The prosthesis as defined in claim 5 wherein the shell has a means for securing itself to the acetabulum.

8. The prosthesis as defined in claim 5 wherein the outside surface of the shell is substantially spherical.

9. The prosthesis as defined in claim 5 wherein the vertical slot forms two fingers of substantially equal length.

10. The prosthesis as defined in claim 9 wherein the fingers are each provided with a bore through the bottom surface for insertion of an instrument to move the fingers closer together.

* * * * *